United States Patent [19]
Yu et al.

[11] Patent Number: 5,360,615
[45] Date of Patent: *Nov. 1, 1994

[54] SOLVENT SYSTEM ENHANCING THE SOLUBILITY OF PHARMACEUTICALS FOR ENCAPSULATION

[75] Inventors: Man S. Yu, Rochester, N.Y.; Foo S. Hom, Safety Harbor; Sibaprasanna Chakrabarti, Oldsmer, both of Fla.; Chong-Heng Huang, Madison, N.J.; Mahendra Patel, Swindon, England

[73] Assignee: R. P. Scherer Corp., Troy, Mich.

[*] Notice: The portion of the term of this patent subsequent to Dec. 10, 2008 has been disclaimed.

[21] Appl. No.: 890,285

[22] Filed: May 26, 1992

Related U.S. Application Data

[63] Continuation of Ser. No. 642,187, Jan. 16, 1991, abandoned, which is a continuation of Ser. No. 104,911, Oct. 9, 1987, Pat. No. 5,071,643, which is a continuation-in-part of Ser. No. 920,577, Oct. 17, 1986, abandoned.

[51] Int. Cl.$^5$ .............. A61K 9/08; A61K 9/48; A61K 9/20; A61K 47/34
[52] U.S. Cl. .................... 424/455; 424/456; 424/465; 514/772.7
[58] Field of Search ............ 424/80, 78, 455, 456; 514/772.7

[56] References Cited

U.S. PATENT DOCUMENTS

| | | | |
|---|---|---|---|
| 3,557,280 | 1/1971 | Weber et al. | 424/80 |
| 3,849,549 | 11/1974 | Dempski et al. | 514/420 X |
| 3,851,051 | 11/1974 | Miskel et al. | |
| 4,002,718 | 1/1977 | Gardella et al. | 424/455 |
| 4,145,440 | 3/1979 | Fitch et al. | 514/570 |
| 4,472,376 | 9/1984 | Kamishita | 514/944 X |
| 4,486,412 | 12/1984 | Shah et al. | 424/456 |
| 4,525,348 | 6/1985 | Arizono et al. | 424/81 |
| 4,690,823 | 9/1987 | Lohner et al. | 424/456 |
| 4,701,327 | 10/1987 | Henmi et al. | 424/455 |
| 4,708,834 | 11/1987 | Cohen et al. | 424/455 |
| 4,713,246 | 12/1987 | Begum et al. | 424/455 |
| 4,798,725 | 1/1989 | Patel | 424/456 |

FOREIGN PATENT DOCUMENTS

| | | | |
|---|---|---|---|
| 0086468 | 2/1982 | European Pat. Off. | |
| 0070714 | 7/1982 | European Pat. Off. | 514/570 |
| 2079600 | 1/1982 | United Kingdom | 514/570 |
| 2096890 | 10/1982 | United Kingdom | 514/420 |
| WO85/03439 | 8/1985 | WIPO | 514/629 |

*Primary Examiner*—Edward J. Webman
*Attorney, Agent, or Firm*—Allegretti & Witcoff, Ltd.

[57] ABSTRACT

This invention relates to a solvent system for enhancing the solubility of an acidic, basic, or amphoteric pharmaceutical agent to produce a highly concentrated solution suitable for softgel filling or two piece encapsulation. The solvent system comprises polyethylene glycol containing 0.2-1.0 mole equivalents of an ionizing agent per mole equivalent pharmaceutical agent and 1-20% water. Glycerin or polyvinylpyrrolidone may be added to further enhance the solubility of certain drugs. The disclosed solvent system is capable of enhancing solubilities of pharmaceutical agents 40-400%.

The ionizing agent functions by causing partial ionization (neutralization) of the free pharmaceutical agent. When the pharmaceutical agent is acidic, the ionizing agent is preferably a hydroxide ion species, whereas when the pharmaceutical agent is basic, the ionizing agent is preferably a hydrogen ion species. For amphoteric pharmaceutical agents, either hydroxide ion or hydrogen ion sources may be utilized to effect partial ionization.

The disclosed solvent system is useful because it not only provides for the enhancement or improvement of bioavailability of acidic, basic and amphoteric pharmaceutical agents by delivering them already in solution, but it also provides for a highly concentrated solution capable of encapsulation in a small enough vessel to permit easy swallowing.

The highly concentrated solid solutions of the present invention are also useful for conversion into tablets and as veterinary spot and pour on preparations.

19 Claims, No Drawings

SOLVENT SYSTEM ENHANCING THE SOLUBILITY OF PHARMACEUTICALS FOR ENCAPSULATION

This application is a continuation of application Ser. No. 07/642,187, filed Jan. 16, 1991, abandoned, which is a continuation of application Ser. No. 07/104,911, filed Oct. 9, 1987, now U.S. Pat. No. 5,071,643, which is a continuation-in-part of application Ser. No. 06/920,577, filed Oct. 17, 1986, abandoned.

BACKGROUND OF THE INVENTION

1. Field of the Invention

This invention relates to a novel solvent system for enhancing the solubility of pharmaceutical agents by partial ionization to produce highly concentrated primarily non-aqueous water miscible solutions of those agents; which as liquids are suitable for encapsulation in both softgels (previously known as soft elastic gelatin capsules) and in two piece hard gelatin shells, which can be sealed to retain liquid; which as semi-solids are suitable for encapsulation in two-piece hardshell capsules; and which as solid solutions are suitable for conversion into tablets. The solvent system of the present invention is useful in that it provides for the encapsulation of a pharmaceutical agent in a volume of solution that is small enough to permit easy swallowing. It further provides for the preparation of highly concentrated solutions of a pharmaceutical agent having utility for pour on and spot on preparations in veterinary medicine.

Filled one-piece softgels have been widely known and used for many years and for a variety of purposes. Because softgels have properties which are quite different from telescoping two-piece hardshell capsules, the softgels are capable of retaining a liquid fill material. The fill material may vary from industrial adhesives to bath oils. More commonly, the softgels are used to enclose or contain consumable materials such as vitamins and pharmaceuticals in a liquid vehicle or carrier.

Generally, not all liquids are suitable as vehicles or carriers for enclosing softgels. For example, water, propylene glycol, glycerin and low molecular alcohols, ketones, acids, amines and esters cannot be filled in softgels by themselves and can only be present in small amounts. In particular, concentrations of water greater than 20% will dissolve the gelatin shell. Liquids that are suitable for filling softgels vary from water immiscible liquids such as vegetable oils, aromatic oils, aromatic and aliphatic hydrocarbons, chlorinated hydrocarbons, ethers and esters, to water miscible nonvolatile liquids, such as polyethylene glycols and nonionic surfactants.

There are specified limitations to the use of certain liquids as fill vehicles for softgels. For example, the pH of the fill liquid should not be below 2.5 or above 7.5. At pH's below 2.5, the gelatin is hydrolyzed causing leaking, whereas at pH's greater than 7.5, the gelatin is tanned resulting in decreased solubility of the gelatin shell. Moreover, emulsions of oil/water or water/oil are not suitable for softgel encapsulation because they eventually break up releasing water which dissolves the gelatin shell.

Vitamins and pharmaceuticals that naturally occur as liquids are ideally suited for softgels. These naturally occurring liquids are simply mixed with a miscible liquid carrier which is also suited as a softgel fill.

Vitamins and pharmaceuticals that naturally occur as solids may be filled into softgels in liquid form under primarily one of two approaches—either as a suspension of the solid in a liquid carrier or as a solution of the pharmaceutical agent in the appropriate solvent. Each approach has its attendant problems. For example, in the suspension, the solids must have a particle size no greater than 80 mesh. Coarser materials prevent the softgel filling equipment from functioning properly. They also prevent the achievement of a good "content uniformity" throughout the batch.

By contrast, a solution provides the best liquid form to obtain optimal "content uniformity" in a batch. In addition, a solution provides a faster and more uniform absorption of a pharmaceutical agent than does a suspension. Because of these distinct technical advantages, the solution is preferred over the suspension.

However, a problem in the art is that an appropriate solution of the pharmaceutical agent cannot always be achieved. One constraint is size. Often, it is not possible to dissolve the pharmaceutical agent in a volume of solvent small enough to produce a softgel that is appropriate from the standpoint of economics and patient acceptance. Another constraint, is the solvent itself. The solvent must have sufficient solvating power to dissolve a large amount of the pharmaceutical agent to produce a highly concentrated solution, and yet not hydrolyze, dissolve, or tan the softgel.

It is a primary object of the present invention to provide a solvent system which is capable of producing highly concentrated solutions of pharmaceutical agents and that these highly concentrated solutions be suitable for filling into softgels.

Like the one-piece softgels, the two-piece telescoping hardshell capsules have also been used for many years and for a variety of purposes. Unlike the one-piece softgels, the two piece capsules are not a sealed system and hence are generally not suited for handling liquids. However, a two-piece capsule can handle a liquid without leaking provided that it is properly sealed or that the liquid is converted into a solution which is either solid or semi-solid at room temperature. If the solid or semi-solid solution contained within the two-piece capsule is a highly concentrated solution of a pharmaceutical agent, then the advantages possessed by a solution over a suspension are made available to both the user and the manufacturer. Specifically, the advantage of a faster and more uniform absorption of the pharmaceutical agent is available to the user of the two-piece capsule, while the advantage of uniformity of the batch is available to the capsule manufacturer.

It is a further object of the present invention to provide a solvent system that is capable of producing highly concentrated solutions of pharmaceutical agents that are solid or semi-solid solutions at room temperature and that these solutions also be suitable for two-piece hardshell encapsulation. The highly concentrated solutions that are solid at room temperature have the additional utility of being suitable for conversion into tablets.

Because most pharmaceutical agents are acidic, basic, or amphoteric in nature, it is a further object of this invention to provide a solvent system (pharmaceutical carrier system) which with minor modification could be equally useful for a pharmaceutical agent regardless of its basic, acidic, or amphoteric nature.

Producing a highly concentrated solution of any acidic amphoteric or basic pharmaceutical agent is useful because it permits the encapsulation of a unit dose of the pharmaceutical agent in a softgel or two-piece capsule that is small enough to permit easy swallowing. Filling of a unit dose in a small softgel or 2-piece capsule to permit easy swallowing is useful because it increases patient acceptance of the medication. Patient acceptance is especially important in the case of prescription medications, because patient acceptance of the medication is a substantial step towards solving one of the major problems of prescription drug therapy—patient noncompliance with the prescribed regimen. A further utility of the disclosed solvent system is enhancement of bioavailability of the dissolved pharmaceutical agent. Enhanced bioavailability occurs as a result of delivering the pharmaceutical agent already in solution at the site of absorption, permitting a faster and more uniform absorption to occur.

2. Description of Related Art

Weber and Molenaar U.S. Pat. No. 3,557,280, teaches the preparation of aqueous solutions of oxytetracycline suitable for intramuscular and intravenous injection or for administration as a syrup in pediatric cases. The Weber and Molenaar (Weber) invention consists of dissolving oxytetracycline in water, in which a given quantity of polyvinylpyrrolidone has been dissolved, to which has been added a suitable quantity of magnesium salt, the pH of which has been adjusted to between 8.0-9.5 using a base such as sodium hydroxide, ammonia, etc.

Although Weber uses polyvinylpyrrolidone to enhance the solubility of oxytetracycline in an aqueous system, Weber neither teaches nor suggests that polyvinylpyrrolidone would also be useful for enhancing solubility of other pharmaceutical agents in non-aqueous systems. Moreover, the aqueous solutions taught by Weber are totally unsuited for either softgel or two-piece encapsulation, since such aqueous solutions would dissolve the gelatin shells.

The present invention differs from Weber in a number of other respects as well. Whereas Weber teaches the formation of relatively dilute solutions (1-20%), the present invention teaches the preparation of more highly concentrated solutions (30-80%) requiring more skill than that disclosed in Weber.

Whereas Weber teaches at column 3, line 25 that a salt suitable for chelating, such as magnesium, is "essential" to enhance the solubility of oxytetracycline, the present invention teaches the preparation of highly concentrated non-aqueous solutions of pharmaceutical agents without resorting to chelate formation to enhance solubility.

Although both Weber and the present invention use the base, sodium hydroxide, in the preparation of their pharmaceutical formulations, the role played by the sodium hydroxide in each invention differs. Whereas Weber uses the sodium hydroxide to adjust the pH to between 8.0-9.5 as to increase the shelf life of the oxytetracycline solution (see Merck Index, 9th edition at p. 904), the present invention uses the sodium hydroxide to enhance the solubility of an acidic pharmaceutical agent by forming as much of the ionized form of the acidic agent as is capable of being solvated by the system.

Gardella et al, U.S. Pat. No. 4,002,718, teaches at column 3, line 47, the use of small amounts of polyvinylpyrrolidone or glycerin to hasten dissolution of micronized digoxin in a liquid vehicle, polyethylene glycol, to form a solution suitable for softgels. Unlike Gardella, which only teaches the use of polyvinylpyrrolidone or glycerin as a formulatory agent to hasten or speed up dissolution, the present invention teaches the use of glycerin or polyvinylpyrrolidone to enhance or increase the amount of the pharmaceutical agent that is soluble in a given volume of liquid.

In further contrast, Gardella only teaches the production of very dilute solutions (0.1%) for encapsulation, whereas the present invention teaches the production of highly concentrated solutions (30-80%). Because the solutions of the present invention are 300-800 times more concentrated than that taught by Gardella, the teachings of Gardella are not applicable to the present invention. Moreover, Gardella does not even suggest that glycerin, propylene glycol, or polyvinylpyrrolidone would be useful for enhancing solubilities of pharmaceutical agents as to produce 30-80% solutions of those agents.

Wagner, U.S. Pat. No. 4,562,192, suggests the use of polyvinylpyrrolidone as a formulatory agent (adjuvant) for pharmaceutical preparations. However, Wagner neither teaches nor suggests that polyvinylpyrrolidone is useful for enhancing the solubility of a pharmaceutical agent in a given volume of liquid.

SUMMARY OF THE INVENTION

The present invention generally relates to a pharmaceutical carrier system ("solvent system") for enhancing the solubility of any acidic, basic, or amphoteric pharmaceutical agent by partial ionization to produce a highly concentrated primarily non-aqueous solution suitable for filling softgels or for two piece encapsulation or for tablet formation, the solvent system comprising in its simplest form 10-80% by weight polyethylene glycol, a solubility enhancing amount of either hydroxide or hydrogen ion and 1-20% by weight of water.

In particular, the present invention relates to a solvent system for enhancing the solubility of an acidic pharmaceutical agent to produce a highly concentrated solution suitable for softgel filling comprising 10-80% polyethylene glycol, a solubility enhancing amount of hydroxide ion, preferably 0.2-1.0 mole equivalents of hydroxide ion per mole equivalent of acid in an acidic pharmaceutical agent, and 1-20% by weight of water.

In addition, the present invention also relates to a simple modification of the disclosed solvent system wherein hydrogen ion is substituted for hydroxide ion, thereby enhancing the solubility of any basic pharmaceutical agent in polyethylene glycol so as to produce a highly concentrated solution of the basic pharmaceutical agent which is also suited for softgel filling, encapsulation or tablet formation.

The polyethylene glycol used herein has an average molecular weight of between about 200-100,000 daltons (hereinafter, all molecular weights are expressed in daltons). Moreover, the weight of polyethylene glycol selected affects the type of solution produced. Polyethylene glycol having an average molecular weight from about 200-800, preferably from about 400-700, and most preferably about 600, produces a softgel fill solution that is a liquid. Polyethylene glycol having an average molecular weight from about 800-10,000, preferably from about 2,000-8,000, produces a softgel fill solution that is semi-solid, and polyethylene glycol having an average molecular weight between about 10,000-100,000, preferably about 15,000-60,000, produces a softgel fill solution that is solid.

Contemplated equivalents of polyethylene glycol include analogs, such as the polyethylene glycol ethers of various alcohols including but not limited to tetraglycol—the polyethylene glycol ether of tetrahydrofurfuryl alcohol, and copolymers of polyethylene glycol.

Further enhancement of the solubility of the pharmaceutical agent in polyethylene glycol is accomplished by the addition of 4–12% by weight of glycerin or propylene glycol and/or by the further addition of 1–20% by weight of polyvinylpyrrolidone, said polyvinylpyrrolidone preferably having an average molecular weight between about 10,000–100,000.

For the acidic pharmaceutical agents, it is preferred that the concentration of liquids with hydroxyl ions, such as glycerin, ethanol, propylene glycol be kept as low as possible. In contrast, the concentration of water in the solvent system should be as high as possible.

The present invention further relates to highly concentrated solutions of the acidic pharmaceutical agents ibuprofen, naproxen, indomethacin, and acetaminophen suitable for filling softgels or two piece capsules, or for tablet formation;

said solution of ibuprofen comprising 40–80% by weight ibuprofen, 0.1–1.5 moles of hydroxide ion per mole of ibuprofen, 1–20% by weight water, and 4–12% by weight glycerin or propylene glycol in polyethylene glycol, wherein said hydroxide ion is more preferredly in the range of 0.2–0.5 moles of hydroxide ion per mole of ibuprofen;

said solution of naproxen comprising 20–50% by weight naproxen, 0.2–0.9 moles of hydroxide ion per mole of naproxen and 1–20% by weight water in polyethylene glycol, wherein said hydroxide ion is more preferredly in the range of 0.4–0.6 moles of hydroxide ion per mole of naproxen;

said solution of indomethacin comprising 30–60% by weight indomethacin, 0.5–1.0 moles of hydroxide ion per mole of indomethacin, and 1–20% by weight water in polyethylene glycol; and said solution of acetaminophen comprising 25–40% by weight acetaminophen, 0.4–1.0 moles of hydroxide ion per mole of acetaminophen, and 1–20% by weight water in polyethylene glycol.

The solubility of the above mentioned acidic pharmaceutical agents in said solutions is further enhanced 2–10% by the further addition of 3–10% by weight of glycerin, or propylene glycol or 1–20% by weight of polyvinylpyrrolidone; the higher percentages (>5%) of polyvinylpyrrolidone being more suited for use in suppositories, two piece capsules, and tablet formation.

The present invention also relates to unit dose forms of ibuprofen, naproxen, indomethacin, and acetaminophen comprising either a softgel or two piece capsule or a tablet containing within a therapeutically effective amount of the appropriate highly concentrated solution of said pharmaceutical agent as disclosed above.

Exactly as was disclosed for the acidic pharmaceutical agents, selection of the polyethylene glycol solvent in the disclosed molecular weight ranges enables the production of liquid semi-solid and solid solutions of the basic pharmaceutical agents.

By way of example, said basic pharmaceutical agents include but are not limited to cimetidine, ranitidine, and nifedipine.

Finally, the present invention relates to a solvent system for enhancing the solubility of amphoteric pharmaceutical agents wherein either hydrogen or hydroxide ions can be used to enhance the solubility of the amphoteric agent by partially ionizing it in the polyethylene glycol systems just described.

This invention further relates to a modification of the disclosed system wherein the ionizable species of the pharmaceutical agent of interest is added directly to polyethylene glycol systems in the form of its pharmaceutically acceptable salt. By selecting the proper ratio of the free pharmaceutical agent and its salt, the solubility of that agent can be maximized.

DETAILED DESCRIPTION

The invention encompasses a solvent system for preparing highly concentrated solutions of pharmaceutical agents wherein the prepared solutions are particularly suitable for softgel filling. The pharmaceutical agents suitable for use with the solvent system of this invention are either acidic, basic or amphoteric compounds, i.e., compounds that are readily ionizable.

Specific examples employing the disclosed solvent system are given for four acidic pharmaceutical agents, indomethacin, ibuprofen, naproxen and acetaminophen. By varying the acidic pharmaceutical agent and by employing the solvent system taught in this invention, one of ordinary skill in the art could produce a highly concentrated solution of any acidic pharmaceutical agent and said concentrated solution would be suitable for filling into softgels.

The present solvent system uses polyethylene glycol (PEG) as its base, preferably having an average molecular weight between about 200–100,000, and most preferably having an average molecular weight between about 400–600 for liquid fills, between about 800–10,000 for semi-solid fills, and between 10,000–100,000 for solid fills. Non-ionized acidic pharmaceutical agents have some solubility in polyethylene glycol, utilizing the solvents hydrophobic binding sites. However, this solubility alone is insufficient to produce a highly concentrated solution which would permit encapsulation of a unit dose in a softgel that would be small enough to permit easy swallowing. For example, Table 1 lists solubilities of the acidic pharmaceutical agents, ibuprofen, naproxen, indomethacin and acetaminophen in polyethylene glycol and the corresponding minimum softgel capsule size required to encapsulate a unit dose as a clear solution. Table 1 further lists the enhanced solubilites of the same pharmaceutical agents in the disclosed solvent system and the corresponding reduced softgel size. In the disclosed solvent system, the enhancement in solubility is presumably due in part to the further ability of the solvent, polyethylene glycol, to utilize separate hydrophilic binding sites to solvate the ionized (hydrophilic) species of the pharmaceutical agent.

TABLE 1

SOLUBILITIES AND CAPSULE SIZE FOR UNIT DOSES OF SOME ACIDIC PHARMACEUTICAL AGENTS IN POLYETHYLENE GLYCOL AND IN THE DISCLOSED SOLVENT SYSTEM

| Agent | Unit Dosage (mg) | Using Polyethylene Glycol 600 | | Using the Disclosed Solvent System | |
|---|---|---|---|---|---|
| | | Solubility (%) | Minimum Capsule Size* | Solubility (%) | Minimum Capsule Size |
| Ibuprofen | 200 | 23 | 14 oblong | 67 | 5 oblong |
| Naproxen | 250 | 15 | 20 oblong | 40 | 7 oblong |
| Indomethacin | 25 | 25 | 1 round | 35 | 1 round |
| Acetaminophen | 500 | 25 | 30 oval | 35 | 20 oval |

*minimum capsule size for a clear fill as a solution and not as a suspension.

Thus, the present solvent system enhances the solubility of acidic pharmaceutical agents in polyethylene glycol by increasing the number of species of the acidic agent (ionized and unionized) that are available to go into solution and by providing adequate solvation for each species. The present solvent system accomplishes this increase in solubility by utilizing both the hydrophobic and hydrophilic binding sites in polyethylene glycol; and by further employing a combination of adjunctive devices which act complementary to one another producing an overall solubility that is greater than could be produced by the addition of any one alone. The adjunctive devices employed in the present invention include hydroxide ion, water, glycerin, and/or polyvinylpyrrolidone.

In the present solvent system in its simplest form comprising polyethylene glycol, sodium hydroxide, and water, the polyethylene glycol acts to dissolve the free form of the acidic agent in monomer, dimer, trimer, etc. form; the sodium hydroxide is present in sufficient quantity to only partially form the sodium salt of the acidic pharmaceutical agent; and the small amount of water present acts to form a solvation sphere around the acid salt permitting it to go into solution in the polyethylene glycol.

Table 2 shows the cumulative effect of the addition of several of the adjunctive devices on the solubility of ibuprofen in PEG 600—polyethylene glycol having an average molecular weight of 600. As Table 2 suggests, the combination of hydroxide ion and water in PEG 600 produces a 67% solution of ibuprofen versus a 23% solution for PEG 600 without adjuncts. This is a 44% overall enhancement in solubility produced by the present solvent system.

A similar result is found for the other three acidic pharmaceutical agents tested in this experiment and there is no reason to believe that the combination of hydroxide ion and water would not produce an analogous enhancement of solubility in PEG for other acidic pharmaceutical agents not tested in this invention.

TABLE 2

EFFECT OF ADJUNCTIVE DEVICES ON THE SOLUBILITY OF IBUPROFEN IN PEG 600

| Ibuprofen (mg) | PEG 600 (mg) | Glycerin (wt %) | Water (wt %) | M/E OH* | Ibuprofen Solubility |
|---|---|---|---|---|---|
| 200 | 870 | 0 | 0 | 0 | 23% |
| 200 | 100 | 0 | 4.5 | 0.3 | 61% |
| 402 | 100 | 3.3 | 6.4 | 0.3 | 67% |

*M/E = moles of hydroxide ion for each mole of acidic drug.

The addition of sodium hydroxide and water to ibuprofen (Table 3), or to naproxen, indomethacin, or acetaminophen in polyethylene glycol (PEG) increases the solubility of that pharmaceutical agent up to a certain point. The further addition of sodium hydroxide beyond this point has the reverse effect and causes the pharmaceutical agent to precipitate out of solution as the sodium salt. The optimal amount of sodium hydroxide—the amount of sodium hydroxide producing maximum solubility of the acidic pharmaceutical agent in polyethylene glycol—was in all cases tested less than 1 mole of sodium hydroxide for each mole of acid in the acidic drug, i.e., the NaOH concentration was always less than 1 mole equivalent. In the specific case of ibuprofen in PEG 400 (Table 3), the solubility was maximal (47%) when the sodium hydroxide was present at a mole equivalent of about 0.3 (0.3 moles of sodium hydroxide/mole of the monoacid compound ibuprofen).

TABLE 3

EFFECT OF SODIUM HYDROXIDE ON THE SOLUBILITY OF IBUPROFEN IN PEG 400

| Ibuprofen (mg) | Polyethylene Glycol 400 (mg) | Sodium Hydroxide (M/E) | Water (wt %) | Appearance (Room temp) |
|---|---|---|---|---|
| 200 | 200 | 0.1 | 1.5 | Insoluble (slight ppt) |
| 200 | 200 | 0.2 | 2.8 | Soluble |
| 200 | 200 | 0.3 | 4.1 | Soluble |
| 200 | 200 | 0.4 | 5.2 | Soluble |
| 200 | 200 | 0.5 | 6.6 | Insoluble (solid admixture) |

An unexpected result was obtained when potassium hydroxide was substituted for sodium hydroxide in the preceding discussion. At equimolar concentrations of hydroxide ion, the solubility of ibuprofen, naproxen, indomethacin and acetaminophen was greater in the presence of potassium hydroxide than in the presence of sodium hydroxide. Moreover, much greater concentrations of potassium hydroxide than sodium hydroxide could be utilized to prepare the highly concentrated solutions of the acidic pharmaceutical agents in polyethylene glycol without precipitation occurring. For example, in the case of ibuprofen in PEG 400, precipitation occurs in the presence of 0.5 or more mole equivalents of sodium hydroxide, whereas no precipitation occurs in the presence of 1.0 mole equivalents of potassium hydroxide even at 4° C. (Table 4). Accordingly, potassium hydroxide is the preferred form of hydroxide ion not only because it enhances the solubility of an acidic pharmaceutical agent to a greater extent than sodium hydroxide but also because it is less likely to result in precipitation over a wide variety of concentration ranges even at low temperatures (4° C.) as may occur during shipping.

The above result is very likely explainable based upon the relative sizes of the sodium and potassium ions. The potassium ion is larger than the sodium ion. Hence, the charge on the potassium ion is dispensed over a larger area causing it to require less solvation thereby permitting more solvation for other species. Accordingly, any hydroxide species, with a pharmaceutically acceptable cation as large or larger than potassium, such as ammonium and the like, should be equally or more suited to producing a highly concentrated solution of an acidic pharmaceutical agent.

If one wishes to further enhance solubility an additional 2–10% beyond that produced by the polyethylene glycol, hydroxide ion, and water system, it is necessary to either add glycerin and propylene glycol or polyvinylpyrrolidone or both to the disclosed system. Glycerin is especially effective in enhancing the solubility of ibuprofen when present in a preferred concentration range of 3–12% by weight. The concentration range most preferred being 4–8% by weight.

Polyvinylpyrrolidone enhances the solubility of acidic pharmaceutical agents when present in the disclosed system in a concentration range of 1–20%. The preferred average molecular weight for the polyvinylpyrrolidone is 10,000–100,000. The addition of polyvinylpyrrolidone to the present system can serve a dual function. Not only does the polyvinylpyrrolidone enhance solubility as to enable production of a highly concentrated solution suitable for filling softgels, but it is also useful for enabling production of a highly viscous as well as a highly concentrated solution suitable for filling a softgel where use is intended as a vaginal or rectal suppository. Although solubility is enhanced by polyvinylpyrrolidone over the entire molecular weight range as disclosed, the polyvinylpyrrolidones at the high molecular weight end of the range are preferred for use in the preparation of suppositories.

The use of either the higher molecular weight polyvinylpyrrolidones or the higher molecular weight polyethylene glycols at a concentration of 5-10% by weight permits the production of a highly concentrated solution of an acidic pharmaceutical agent that is a semisolid or solid solution at room temperature and thereby is suitable for two-piece encapsulation without leaking. The solid solutions have an additional utility in that they can even be converted into tablets by processes known to those skilled in the art.

Using the disclosed solvent system, it is possible to prepare a unit dose of any acidic pharmaceutical agent by enclosing a highly concentrated solution of the acidic pharmaceutical agent in a softgel or two piece capsule, wherein the fill solution (liquid or solid) contains a therapeutically effective amount of acidic pharmaceutical agent dissolved within. The dosages administered will vary depending upon the acidic pharmaceutical agent employed, the mode of administration, the treatment desired, the size, age, and weight of the patient being treated and the like.

Aside from the solubility enhancing adjuvants already disclosed, the highly concentrated solutions of this invention may also contain suitable preserving, stabilizing, or wetting agents, and coloring substances. Pharmaceutically acceptable preservatives include for example benzyl alcohol and the like.

By substituting hydrogen ion for hydroxide ion, the disclosed solvent system is modified to enhance the solubility of basic pharmaceutical agents in polyethylene glycol so as to provide highly concentrated solutions of the basic pharmaceutical agents which are suited for filling softgels, encapsulation, or tablet formation. As an example, the basic drug, thioridazine was insoluble in PEG 400 at temperatures slightly below room temperature, whereas thioridazine in the presence of hydrogen ion was soluble in PEG 400 even when the temperature was dropped to $-5°$ C. (Table 4).

TABLE 4

SOLUBILITY OF THE BASIC DRUG THIORIDAZINE IN PEG 400 IN THE PRESENCE AND ABSENCE OF HYDROGEN ION

| INGREDIENTS | FORMULA I (mg) | FORMULA II (mg) |
| --- | --- | --- |
| Thioridazine | 25.0 | 25.0 |
| Hydrochloric Acid | 0.0 | 2.4 |
| Water | 8.0 | 8.0 |
| Polyethylene Glycol 400 | 150.0 | 150.0 |
| Propylene Glycol | 12.0 | 12.0 |
| Alcohol, (USP) | 8.0 | 8.0 |
| Povidone (polyvinylpyrrolidone) | 5.0 | 5.0 |
| RESULT at 5° C. | INSOLUBLE | SOLUBLE |

By way of further example, basic pharmaceutical agents suited for forming the highly concentrated solutions of this invention include but are not limited to cimetidine, ranitidine, and nifedipine. Pharmaceutically acceptable sources of hydrogen ion include the mineral acids such as hydrochloric, hydrobromic, and sulfuric, and the organic acids such as fumaric, maleic, tartaric, (methane-, ethane-, and benzene) sulfonates, citric, and malic.

The contribution to enhanced solubility made by each component of the disclosed solvent system is apparent from Table 5, where the maximal solubility of the basic pharmaceutical agent, cimetidine, is reported in stepwise fashion from polyethylene glycol through the disclosed systems.

TABLE 5

CONTRIBUTIONS TO ENHANCED SOLUBILITY OF CIMETIDINE MADE BY COMPONENTS OF THE DISCLOSED SOLVENT SYSTEM

| Solvent System | Solvent Proportions (%) | Maximal Solubility of Cimetidine (wt %) |
| --- | --- | --- |
| Polyethylene Glycol 600 | 100 | 8.6% |
| Polyethylene Glycol 600/Glycerin/Water | 85:5:10 | 11.7% |
| Polyethylene Glycol 600/Glycerin/Water/ 0.25 mole equivalents of Hydrochloric Acid | 82:5:12:1 | 21.3% |
| Polyethylene Glycol 600/Glycerin/Water/ 0.26-0.50 mole equivalents of Hydrochloric Acid | 79:5:14:2 | >21.3% |
| Tetraglycol*/ Glycerin/Water/ 1 Mole equivalent of Hydrochloric Acid | 36:20:29:15 | ~50% |

*Tetraglycol is the polyethylene glycol ether of tetrahydrofurfuryl alcohol and one of the equivalents of polyethylene glycol.

The concepts disclosed herein for producing highly concentrated solutions of acidic and basic pharmaceutical agents are equally applicable to amphoteric compounds—compounds possessing the properties of an acid and a base. Examples of an amphoteric pharmaceutical agent suitable for use with this invention are the amino acid, methyldopa and enalapril.

It is also within the scope of this invention to directly add in the appropriate ratio to PEG and water, both the ionizable species (salt) of the pharmaceutical agent and its non-ionized species (free pharmaceutical agent) to produce a highly concentrated solution of the pharmaceutical agent suitable for soft-gel encapsulation. In this way, the use of ionizing agents such as hydroxide or hydrogen ion to produce the desired ratio of ionization (neutralization) of the pharmaceutical is avoided or minimized.

DETAILED DESCRIPTION OF THE PREFERRED EMBODIMENT

The following examples are given by way of illustration only and in no way should be construed as limiting the invention in spirit or in scope, as many modifications in materials and methods will be apparent from this disclosure to those skilled in the art.

EXAMPLE I

Preparation of Highly Concentrated Solutions of Acidic Pharmaceutical Agents

Mixtures were prepared in 10 g quantities by dispersing the acidic pharmaceutical agent in polyethylene glycol or polyethylene glycol and glycerin or polyethylene glycol and polyvinylpyrrolidone or polyethylene glycol, glycerin, and polyvinylpyrrolidone. Aqueous solutions of hydroxide were then added. To facilitate mixing, the mixtures were warmed to 60° C. The mixtures were then permitted to cool to the required temperature, (room temperature or 4° C.), and were occasionally mixed for the next 2-7 days. The resulting mixture was then visually inspected to determine whether the solubility of the acidic pharmaceutical agent in the formulation had been exceeded.

EXAMPLE II

Saturation Solubilities of Acidic Pharmaceutical Agents

Mixtures were prepared as described in Example I except that an excess of the acidic pharmaceutical agent was present and the mixture was continuously agitated for at least 7 days. The mixture was then filtered through a Durapore 0.45M filter and the filtrate analyzed.

Once the saturation solubility of a particular acidic pharmaceutical agent has been determined, one can prepare highly concentrated solutions of that particular agent at or near the saturation point utilizing the protocol described in Example I. The highly concentrated solutions so prepared are then suitable for softgels, or for two piece encapsulation, or for conversion into tablets.

EXAMPLE III

Formulation for a Highly Concentrated Solution of Ibuprofen

The following formulation produces a highly concentrated solution of ibuprofen (67%) and is suitable as a softgel fill:

| Ibuprofen | 402 mg |
|---|---|
| Potassium Hydroxide | 38.4 mg (0.3 mole equivalents) |
| Polyethylene Glycol 600 | 100 mg |
| Water | 38.4 mg (6.4% by wt) |
| Glycerin/or Propylene Glycol | 19.8 mg (3.3% by wt) |
| Total | 598.6 mg |

EXAMPLE IV

Formulation for a Highly Concentrated Solution of Naproxen

The following general formulation produces a highly concentrated solution of naproxen (35.9%) and is suitable as a softgel fill:

| Naproxen | 1 equivalent (35.9% by wt) |
|---|---|
| Potassium Hydroxide | 0.50 mole equivalents as a 50% aqueous solution |
| Polyethylene Glycol 600 | balance |

EXAMPLE V

Formulation for a Highly Concentrated Solution of Indomethacin

The following general formulation produces a highly concentrated solution (34.5%) of indomethacin suitable as a softgel fill:

| Indomethacin | 1 equivalent (34.5% by wt) |
|---|---|
| Potassium Hydroxide | 1.08 mole equivalents |
| Polyethylene Glycol 600 | balance |

EXAMPLE VI

Formulation for a Highly Concentrated Solution of Acetaminophen

The following general formulation produces a highly concentrated solution (35.0%) of acetaminophen suitable as a softgel fill:

| Acetaminophen | 1 equivalent (35% by wt) |
|---|---|
| Potassium Hydroxide | 1 equivalent |
| Polyethylene Glycol 600 | balance |

EXAMPLE VII

Formulation for a Highly Concentrated Solution of Cimetidine

The following formulation produces a highly concentrated solution (50% by weight) of cimetidine suitable as a softgel fill:

| Cimetidine | 50% by weight |
|---|---|
| Hydrochloric Acid | 7.5% by weight |
| Tetraglycol* | 18% by weight |
| Glycerin | 10% by weight |
| Water | 14.5% by weight |

*Tetraglycol is the polyethylene glycol ether of tetrahydrofurfuryl alcohol.

EXAMPLE VIII

Formulation for a Highly Concentrated Solution of Diclofenac Sodium

The following formulation produces a highly concentrated (20% by weight) solution of diclofenac sodium suitable as a softgel fill and having a water content of 8.0% w/w.

| Diclofenac Sodium | 100.0 mg | |
|---|---|---|
| Polyethylene Glycol 600 | 357.7 mg | |
| Hydrochloric Acid (36.5% w/w solution) | 6.5 mg | (0.2 mole equivalent) |
| Water | 35.8 mg | |
| Total | 500.0 mg | |

EXAMPLE IX

Formulation for a Highly Concentrated Semi-Solid Solution of Ibuprofen

The following formulation produces a highly concentrated (34% by weight) semi-solid solution of ibuprofen which is suitable for encapsulation in a hard gelatin capsule.

| Ibuprofen | 206.3 mg | |
|---|---|---|
| Polyethylene Glycol 4000 | 336.3 mg | |
| Polyethylene Glycol 400 | 37.4 mg | |
| Potassium Hydroxide | 20.0 mg | (0.35 mole equivalent |
| Total | 600.0 mg | |

The polyethylene glycol 400 and 4000 were warmed to 60° C. until a clear solution was obtained. The drug and powered potassium hydroxide were dispersed in the melt and stirred for about thirty minutes. This solution was then clarified and filled, at 60° C., into hard-shell capsules.

EXAMPLE X

Formulation for a Highly Concentrated Semi-Solid Solution of Naproxen

The following formulation produces a highly concentrated (43% by weight) semi-solid solution of naproxen which is suitable for encapsulation in a hard gelatin capsule.

| | |
|---|---|
| Naproxen | 260.4 mg |
| Polyethylene Glycol 4000 | 285.4 mg |
| Polyethylene Glycol 400 | 31.7 mg |
| Potassium Hydroxide | 22.5 mg (0.35 mole equivalent |
| Total | 600.0 mg |

The capsules were prepared in a similar manner to the method disclosed in Example XI.

EXAMPLE XI

Formulation for a Highly Concentrated Solid Solution of Naproxen

The following formulation produces a highly concentrated (40% by weight) solid solution of naproxen suitable for producing tablets.

| | |
|---|---|
| Naproxen | 250.0 mg |
| Polyethylene Glycol 20,000 | 338.5 mg |
| Potassium Hydroxide | 18.25 mg (0.3 mole equivalent |
| Water | 18.25 mg |
| Total | 625.0 mg |

The polyethylene glycol 20,000 was heated to 80° C. to produce a clear solution. The drug was then added and with gentle stirring, dispersed. The potassium hydroxide was added in aqueous solution and the mixture stirred until a clear solution was produced. The molten solution was then poured into 16 mm round PVC blisters and allowed to cool to form tablets.

EXAMPLE XII

Formulation for a Highly Concentrated Solution of Ibuprofen

The following formulation produces a highly concentrated (40% by weight) solution of ibuprofen, without using strongly alkaline solutions, which is suitable as a softgel fill.

| | |
|---|---|
| Ibuprofen | 120.0 mg |
| Ibuprofen Sodium | 92.6 mg (0.4 mole equivalent |
| Polyethylene Glycol 600 | 263.6 mg |
| Water | 23.8 mg |
| Total | 500.0 mg |

EXAMPLE XIII

Dissolution Profiles of Semi-Solid Formulations

The dissolution profiles of the formulation described in Example X which had been filled into size 1 hard gelatin capsules was determined using the USP dissolution test (apparatus 1). The basket speed was set at 100 rpm and the dissolution medium used as pH 7 buffer. Release of drug was determined by UV-spectroscopy at the wavelength of maximum absorption. The times for 25, 50 and 70% release of drug are given in the table below.

| Time for % Release | Example IX Ibuprofen |
|---|---|
| 25% | 15.9 min. |
| 50% | 23.3 min. |
| 70% | 29.0 min. |

EXAMPLE XIV

Dissolution Profile of Solid Formulation

The dissolution profile of a tablet of the formulation described in Example XI was compared to a tablet made from the same formulation, but omitting the potassium hydroxide. The USP dissolution test (apparatus 2) was used with the paddle speed set at 100 rpm and a dissolution medium of pH 7 buffer. The tablets were fixed to allow only the top surface to be in contact with the dissolution medium to allow intrinsic dissolution measurements. UV-spectroscopy at the wavelength of maximum absorption was used to quantify drug release. The intrinsic dissolution rate constants were calculated from the slope of the release curve over the initial thirty minutes and are given in the table below.

| Formulation | Dissolution Rate |
|---|---|
| Example XII | 0.74 mg/min/cm$^2$ |
| Example XII without Potassium Hydroxide | 0.41 mg/min/cm$^2$ |

What is claimed is:

1. A pharmaceutically acceptable solution of an acidic pharmaceutical agent suitable for filling softgels and having a pH of 2.5 to 7.5 for subsequent oral administration, comprising the acidic pharmaceutical agent and a solvent system, the solvent system comprising 10% to 80% polyethylene glycol by weight of the solvent system, 1% to 20% water by weight of the solvent system and a hydroxide species, the hydroxide species being capable of dissociating in the solvent system into pharmaceutically acceptable cations and hydroxide ions, the hydroxide species being present in an amount such that between 0.1 and less than one mole of hydroxide ions per mole of acidic groups in the acidic pharmaceutical agent is present in the solution, the hydroxide species partially ionizing the acidic pharmaceutical agent such that the acidic pharmaceutical agent is present in a dissolved state in the solution as both a free acid and a cationic salt, the acidic pharmaceutical agent being present in a dissolved state in the solution in a solubility enhanced amount greater than the maximum amount of the acidic pharmaceutical agent capable of dissolving in the solvent system in the absence of the hydroxide species and less than or equal to 80% by weight of the solution.

2. The solution according to claim 1 further containing 4–12% glycerin by weight of the solvent system.

3. The solution according to claim 2 wherein said polyethylene glycol has an average molecular weight of between about 200–100,000.

4. The solution according to claim 1 wherein the hydroxide species is selected from the group consisting of sodium hydroxide, ammonium hydroxide and potassium hydroxide.

5. The solution according to claim 1 wherein said polyethylene glycol has an average molecular weight of between about 200–100,000.

6. The solution according to claim 5 further containing 1–20% polyvinylpyrrolidone by weight of the solvent system; said polyvinylpyrrolidone having an average molecular weight between about 10,000–100,000.

7. The solution according to claim 1 further containing 1–20% polyvinylpyrrolidone by weight of the solvent system.

8. The solution of claim 1 wherein the acidic pharmaceutical agent is selected from the group consisting of ibuprofen, naproxen, indomethacin, acetaminophen and diclofenac sodium.

9. A pharmaceutically acceptable solution of a basic pharmaceutical agent suitable for filling softgels and having a pH of 2.5 to 7.5 for subsequent oral administration, comprising the basic pharmaceutical agent and a solvent system, the solvent system comprising 10% to 80% polyethylene glycol by weight of the solvent system, 1% to 20% water by weight of the solvent system and a hydrogen ion species, the hydrogen ion species being capable of dissociating in the solvent system into hydrogen ions and pharmaceutically acceptable anions, the hydrogen ion species being present in an amount such that between 0.1 and less than one mole of hydrogen ions per mole of basic groups in the basic pharmaceutical agent is present in the solution, the hydrogen ion species partially ionizing the basic pharmaceutical agent such that the basic pharmaceutical agent is present in a dissolved state in the solution as both a free base and an anionic salt, the basic pharmaceutical agent being present in a dissolved state in the solution in a solubility enhanced amount greater than the maximum amount of the basic pharmaceutical agent capable of dissolving in the solvent system in the absence of the hydrogen ion species and less than or equal to 80% by weight of the solution.

10. The solution according to claim 9 wherein said polyethylene glycol has an average molecular weight of between about 200–800.

11. The solution according to claim 9 wherein 50–95% of the polyethylene glycol has an average molecular weight between about 800 to about 10,000.

12. The solution according to claim 9 wherein the polyethylene glycol has an average molecular weight between about 10,000 to about 100,000.

13. The solution according to claim 9 further containing 1–20% polyvinylpyrrolidone by weight of the solvent system; said polyvinylpyrrolidone having an average molecular weight between about 10,000–100,000.

14. The solution of claim 9 wherein the basic pharmaceutical agent is selected from the group consisting of thioridazine, cimetidine and ranitidine.

15. A pharmaceutically acceptable solution of an amphoteric pharmaceutical agent suitable for filling softgels and having a pH of 2.5 to 7.5 for subsequent oral administration, comprising the amphoteric pharmaceutical agent and a solvent system, the solvent system comprising 10% to 80% polyethylene glycol by weight of the solvent system, 1% to 20% water by weight of the solvent system and an ion species selected from the group consisting of cationic hydroxide species and anionic hydrogen ion species, the ion species being capable of dissociating in the solvent system into pharmaceutically acceptable ions, the ion species being present in an amount such that between 0.1 and less than one mole of ions selected from the group consisting of hydrogen ions and hydroxide ions per mole of ionizable groups in the amphoteric pharmaceutical agent is present in the solution, the ion species partially ionizing the amphoteric pharmaceutical agent such that the amphoteric pharmaceutical agent is present in a dissolved state in the solution both in a free form and a salt form, the amphoteric pharmaceutical agent being present in a dissolved state in the solution in a solubility enhanced amount greater than the maximum amount of the amphoteric pharmaceutical agent capable of dissolving in the solvent system in the absence of the ion species and less than or equal to 80% by weight of the solution.

16. The solution of claim 15 wherein the amphoteric pharmaceutical agent is selected from the group consisting of methyldopa and enalapril.

17. A pharmaceutically acceptable solution of an acidic pharmaceutical agent suitable for two-piece encapsulation or for tablet formation for subsequent oral administration, comprising the acidic pharmaceutical agent and a solvent system, the solvent system comprising 10% to 80% polyethylene glycol by weight of the solvent system, 1% to 20% water by weight of the solvent system and a hydroxide species, the hydroxide species being capable of dissociating in the solvent system into pharmaceutically acceptable cations and hydroxide ions, the hydroxide species being present in an amount such that between 0.1 and less than one mole of hydroxide ions per mole of acidic groups in the acidic pharmaceutical agent is present in the solution, the hydroxide species partially ionizing the acidic pharmaceutical agent such that the acidic pharmaceutical agent is present in a dissolved state in the solution as both a free acid and a cationic salt, the acidic pharmaceutical agent being present in a dissolved state in the solution in a solubility enhanced amount greater than the maximum amount of the acidic pharmaceutical agent capable of dissolving in the solvent system in the absence of the hydroxide species and less than or equal to 80% by weight of the solution.

18. A pharmaceutically acceptable solution of a basic pharmaceutical agent suitable for two-piece encapsulation or for tablet formation for subsequent oral administration, comprising the basic pharmaceutical agent and a solvent system, the solvent system comprising 10% to 80% polyethylene glycol by weight of the solvent system, 1% to 20% water by weight of the solvent system and a hydrogen ion species, the hydrogen ion species being capable of dissociating in the solvent system into hydrogen ions and pharmaceutically acceptable anions, the hydrogen ion species being present in an amount such that between 0.1 and less than one mole of hydrogen ions per mole of basic groups in the basic pharmaceutical agent is present in the solution, the hydrogen ion species partially ionizing the basic pharmaceutical agent such that the basic pharmaceutical agent is present in a dissolved state in the solution as both a free base and an anionic salt, the basic pharmaceutical agent being present in a dissolved state in the solution in a solubility enhanced amount greater than the maximum amount of the basic pharmaceutical agent capable of dissolving in the solvent system in the absence of the hydrogen ion species and less than or equal to 80% by weight of the solution.

19. A pharmaceutically acceptable solution of an amphoteric pharmaceutical agent suitable for two-piece encapsulation or for tablet formation for subsequent oral administration, comprising the amphoteric pharmaceutical agent and a solvent system, the solvent system comprising 10% to 80% polyethylene glycol by weight of the solvent system, 1% to 20% water by weight of the solvent system and an ion species selected from the group consisting of cationic hydroxide species and anionic hydrogen ion species, the ion species being capable of dissociating in the solvent system into pharmaceutically acceptable ions, the ion species being present in an amount such that between 0.1 and less than one mole of ions selected from the group consisting of hydrogen ions and hydroxide ions per mole of ionizable groups in the amphoteric pharmaceutical agent is present in the solution, the ion species partially ionizing the amphoteric pharmaceutical agent such that the amphoteric pharmaceutical agent is present in a dissolved state in the solution both in a free form and a salt form, the amphoteric pharmaceutical agent being present in a dissolved state in the solution in a solubility enhanced amount greater than the maximum amount of the amphoteric pharmaceutical agent capable of dissolving in the solvent system in the absence of the ion species and less than or equal to 80% by weight of the solution.

* * * * *